(12) United States Patent
Valentine

(10) Patent No.: US 8,985,104 B2
(45) Date of Patent: Mar. 24, 2015

(54) FAN ASSEMBLY FOR A REBREATHE SYSTEM

(75) Inventor: Earl Valentine, Yorba Linda, CA (US)

(73) Assignee: CareFusion 207, Inc., San Diego, CA (US)

( * ) Notice: Subject to any disclaimer, the term of this patent is extended or adjusted under 35 U.S.C. 154(b) by 606 days.

(21) Appl. No.: 12/783,016

(22) Filed: May 19, 2010

(65) Prior Publication Data

US 2011/0288428 A1     Nov. 24, 2011

(51) Int. Cl.
| | |
|---|---|
| A61M 16/00 | (2006.01) |
| A62B 7/00 | (2006.01) |
| A61B 5/097 | (2006.01) |
| A61M 16/08 | (2006.01) |
| A61B 5/08 | (2006.01) |
| A61M 16/20 | (2006.01) |
| A61M 16/22 | (2006.01) |

(52) U.S. Cl.
CPC ............ *A61B 5/097* (2013.01); *A61M 16/0045* (2013.01); *A61M 16/0057* (2013.01); *A61M 16/08* (2013.01); *A61M 16/085* (2013.01); *A61M 16/0891* (2013.01); *A61B 5/082* (2013.01); *A61M 16/0078* (2013.01); *A61M 16/208* (2013.01); *A61M 16/22* (2013.01); *A61M 2016/0036* (2013.01); *A61M 2205/11* (2013.01); *A61M 2230/43* (2013.01)
USPC ............ 128/204.19; 128/204.18; 128/205.12; 128/205.17

(58) Field of Classification Search
CPC ...................... A61M 16/0045; A61M 16/0066; A61M 16/0069; A61M 16/0078; A61M 16/0081; A61M 16/0084; A61M 16/22
USPC ............. 128/200.24, 204.18, 204.19, 204.21, 128/205.12, 205.17, 205.28, 914
See application file for complete search history.

(56) References Cited

U.S. PATENT DOCUMENTS

| | | | | |
|---|---|---|---|---|
| 4,299,784 | A * | 11/1981 | Hense | ........................ 261/78.2 |
| 4,478,216 | A | 10/1984 | Dukowski | |
| 5,036,841 | A * | 8/1991 | Hamilton | ................. 128/202.26 |
| 6,523,538 | B1 | 2/2003 | Wikefeldt | |
| 7,670,118 | B2 | 3/2010 | Sato | |
| 2004/0000310 | A1* | 1/2004 | Wickham et al. | ........ 128/204.18 |
| 2004/0103899 | A1* | 6/2004 | Noble | ...................... 128/207.18 |
| 2005/0283089 | A1* | 12/2005 | Sullivan et al. | ............... 600/529 |
| 2009/0107168 | A1 | 4/2009 | Sanders et al. | |
| 2009/0246013 | A1* | 10/2009 | Kenyon et al. | ............. 415/208.2 |
| 2010/0006097 | A1* | 1/2010 | Frater et al. | ............. 128/204.18 |
| 2010/0074777 | A1 | 3/2010 | Laufer et al. | |

OTHER PUBLICATIONS

PCT Search Report mailed Oct. 31, 2011, 9 pgs.

* cited by examiner

*Primary Examiner* — Valerie L Skorupa
(74) *Attorney, Agent, or Firm* — McDermott Will & Emery LLP

(57) ABSTRACT

A circulation system for use in a rebreathe system includes a base and a fan assembly coupled to the base. The base includes a motor and a rotatable drive shaft coupled to the motor. The fan assembly includes a housing with an inlet and outlet. The fan assembly further includes a fan coupled to the drive shaft to rotate therewith and is fluidly isolated from the drive shaft.

14 Claims, 2 Drawing Sheets

FAN ASSEMBLY FOR A REBREATHE SYSTEM

BACKGROUND

During pulmonary function testing, a rebreathe system is employed to perform various measurements of a patient's respiratory system. Current rebreathe circuits include a series of components that include a breathing valve assembly which may include expire- and inspire-only valves, a reservoir, a carbon dioxide absorber, and a circulation fan that pulls air from the reservoir, pushes the air through the carbon dioxide absorber and then back into the reservoir. Alternatively, the circulation fan may also pull air from the carbon dioxide absorber and then push air into the reservoir. A rebreathe circuit supports several pulmonary function tests including, but not limited to, a closed circuit helium functional residual capacity ($FRC_{HE}$) test, a nitric oxide diffusing capacity (DLNO) test, a diffusing capacity of carbon monoxide (DLCO) test, and other tests that are used to diagnose lung function conditions. During the circulation of air, carbon dioxide is removed from the gases as they pass through the carbon dioxide absorber.

Components of rebreathe systems can be single use (i.e., disposable) or multi-use. For multi-use rebreathe systems, these components can be isolated from cross-contamination through the use of a barrier filter and, with or without barrier filters, the components need to be cleaned and disinfected periodically so as to prevent cross-contamination between patients and/or remove contamination particles from the components. Independent of being single use or reusable, cleaning and/or disinfecting of the circulation fans can be particularly problematic. Current fans in rebreathe systems are directly coupled to a fan motor and are cumbersome and time consuming to remove for cleaning of surfaces of the fan. Moreover, electrical components of the motor need protection from cleaning and disinfectant solutions so as to prevent damage thereto. If not properly cleaned, parts of the rebreathe circuit can be exposed to cross-contamination from one patient to the next patient.

SUMMARY

Concepts of the present disclosure relate to a rebreathe system that utilizes a fan fluidly isolated from a motor in order to provide a breathing circuit that can be easily cleaned or inexpensively replaced for elimination of cross-contamination. In one aspect, a circulation system for a rebreathe system includes a base enclosing a motor and a fan assembly coupled to the base. The motor includes a rotatable drive shaft and the fan assembly includes a fan coupled to the drive shaft to rotate therewith and fluidly isolated from the drive shaft. The fan assembly further includes a housing having an inlet and outlet for circulating gas as the fan rotates.

In another aspect, a rebreathe system includes a breathing valve assembly, a reservoir, a circulation system and a carbon dioxide absorber. The breathing valve assembly is configured to be fluidly coupled to a patient and the reservoir stores exhaled gas from the patient. The circulation system includes a fan assembly for circulating air from the reservoir through the carbon dioxide absorber. The fan assembly is rotatably coupled with a motor and fluidly isolated from the motor within the circulation system.

In yet another aspect, a method of performing a pulmonary function test includes receiving exhaled gas from a patient and operating a circulation system to move exhaled gas through a carbon dioxide absorber. The circulation system includes a motor with a drive shaft coupled to a fan assembly. The fan assembly rotates with the drive shaft and is fluidly isolated from the drive shaft.

DETAILED DESCRIPTION

Figure 1:
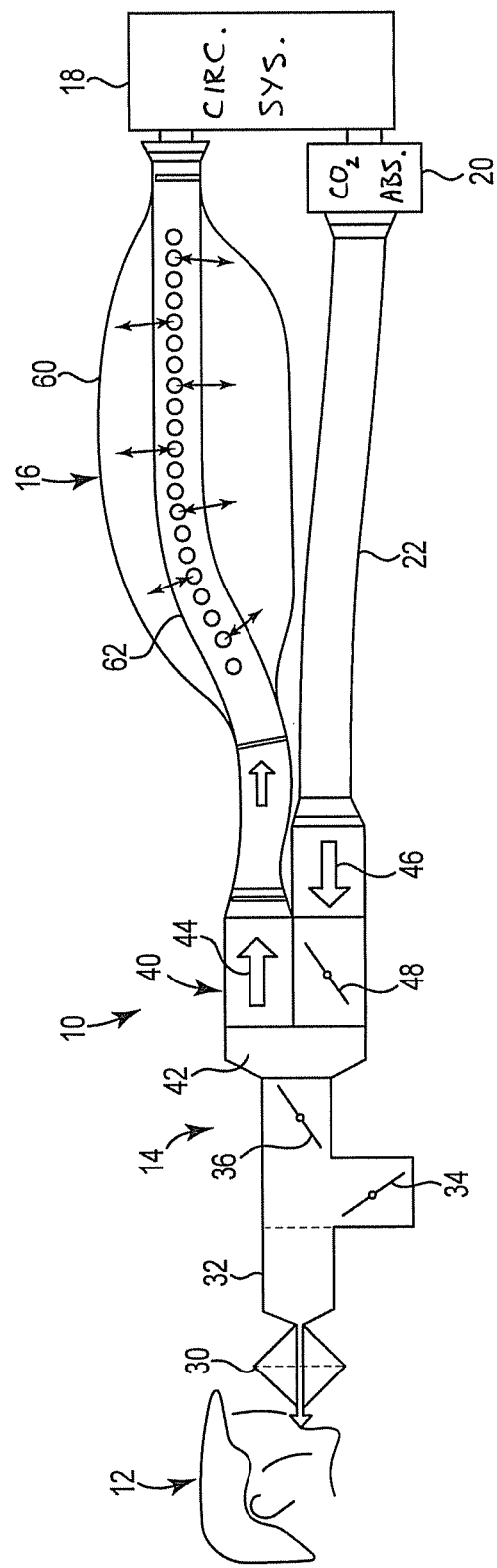
FIG. 1 is a schematic view of a rebreathe system.

FIG. 1 is a schematic diagram of a rebreathe system 10 for testing pulmonary function of a patient 12. The rebreathe system 10 includes a series of components that include a breathing valve assembly 14, a reservoir 16, a circulation control system 18, a carbon dioxide absorber 20 and an inspiration conduit 22. During operation, system 10 is filled with a gaseous mixture. The patient 12 interfaces with the breathing valve assembly 14 and conducts a breathing cycle to inspire and expire the gaseous mixture. Expired gas from the patient travels through the breathing valve assembly 14 to the reservoir 16 and to the circulation system 18, which assists in circulating air through the system 10. Gas then proceeds through the carbon dioxide absorber 20 and to the inspiration conduit 22, ultimately passing back to the patient 12. The patient 12 continues to breathe for an amount of time. A gas analyzer (not shown) can be fluidly coupled to the circulation system 18 (or at other places within system 10) to analyze the gas mixture expired by the patient 12 and then return the analyzed gas to the system 10.

The breathing valve assembly 14 includes an optional filter 30, a flow or volume measuring device 32, an ambient valve 34 opened to allow for the patient to breathe in and out from ambient air and a mixing valve 36 in fluid communication with the remaining components of the rebreathe system 10. When a rebreathe test is active, the ambient valve 34 is closed and the mixing valve 36 is opened, connecting the patient 12 to the rebreathe system 10.

Exhaled air from the patient 12 passes through breathing valve assembly 14 and is transferred into a flow control assembly 40, which includes an adapter 42, a one-way expire-only valve 44, a one-way inspire-only valve 46 and a rebreathe valve 48. Expired gas from the patient 12 passes through adapter 42 and into expire-only valve 44, where the air passes through in a single direction to reservoir 16. Inspiration by the patient comes through inspire-only valve 46, where inspired air passes in a direction opposite from the expire-only valve 44. Rebreathe valve 48 can be used to fill system 10 with a particular gaseous mixture for a desired test. From expire-only valve 44, gas passes through to reservoir 16, where exhaled gases are stored and inspired gases are drawn from during an inspiratory phase of the patient. Reservoir 16 includes a bag 60 for storing exhaled gas and an internal conduit 62 for transmitting the exhaled gas within system 10. Circulation system 18 pulls gas from the reservoir 16, pushing the gas through the carbon dioxide absorber 20, which removes carbon dioxide from the system 10.

The rebreathe system 10 is designed for cleaning and disinfection by a user, whereas patient interface components are made to be disassembled and the components cold soaked in disinfectant liquids. In particular, as discussed below, circulation system 10 includes a fan assembly fluidly isolated from a motor in the circulation system 18 so as to seal and protect the motor from the fan assembly, yet allow for easy removal of the fan assembly for cleaning and disinfecting. In one embodiment, a fan of the fan assembly is magnetically coupled to a drive shaft of the motor to rotate therewith. Once removed from the circulation system 18, the fan assembly can be easily cleaned, for example by soaking the fan assembly in a disinfectant. Moreover, after soaking, the fan assembly can be re-coupled to the motor and the motor can be operated to facilitate drying of the fan assembly.

Figure 2:
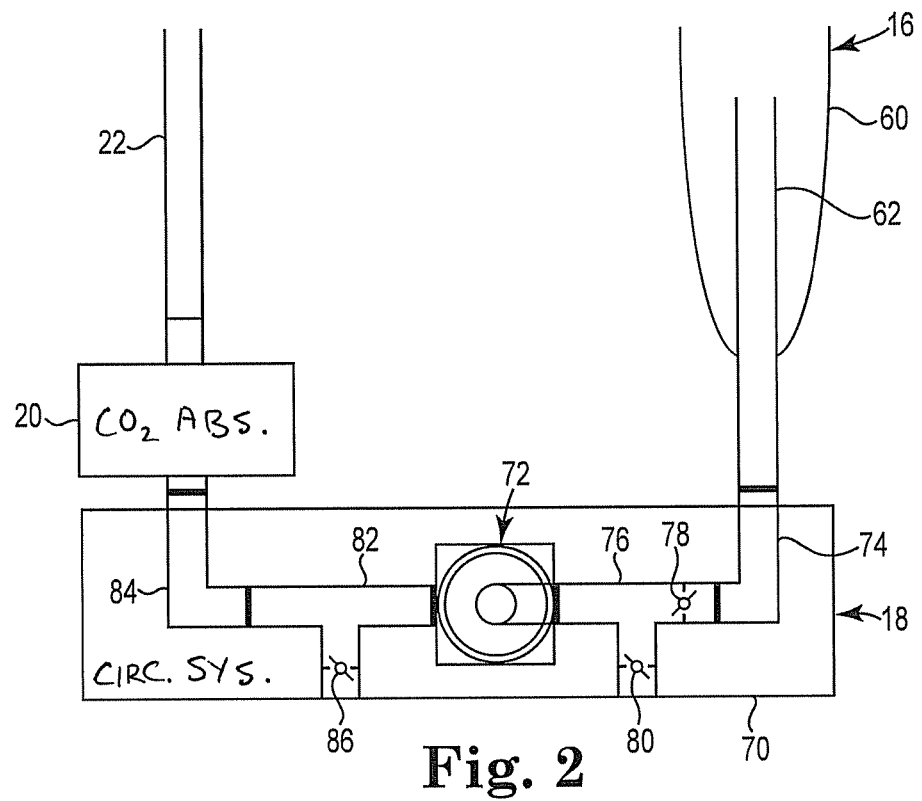
FIG. 2 is a top view of a circulation system.

FIG. 2 illustrates a schematic top view of the circulation system 18. The circulation system 18 includes a base 70 and a fan assembly 72, mounted on the base. Base 70 houses a motor and electronic controls for operation of fan assembly 72, which are otherwise protected due to a separation between the motor and fan assembly 72. Fan assembly 72 is fluidly coupled to the reservoir 16, and in particular conduit 62, through an elbow connector 74 and a T-connector 76. T-connector 76 further maintains a blocking valve 78 and an intake valve 80 for control of gas into and out of rebreathe system 10, for example to fill and/or purge system 10. Fan assembly 72 is fluidly coupled to carbon dioxide absorber 20 through a T-connector 82 and an elbow connector 84. T-connector 82 maintains an exhaust valve 86 for use in purging and/or filling system 10. As is known, the elbow connectors 74 and 84 as well as the T-connectors 76 and 82 can be fluidly coupled together through tapered fittings or o-rings to maintain a seal.

Figure 3:
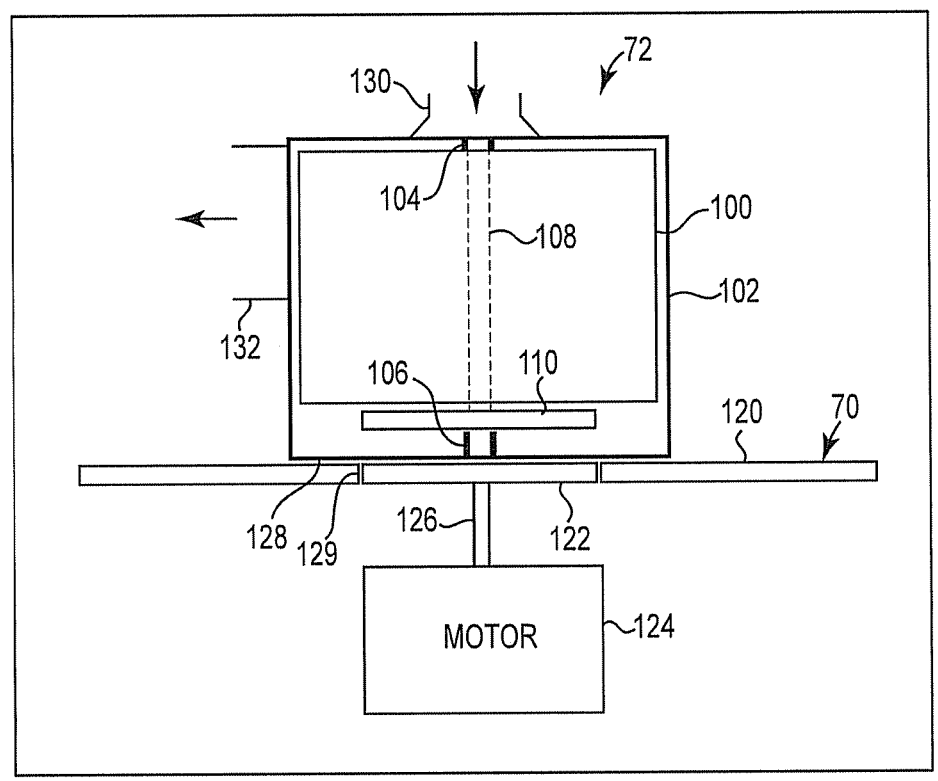
FIG. 3 is a schematic view of a motor and fan assembly of a rebreathe system.

As illustrated in FIG. 3, the fan assembly 72 includes a fan 100, a housing 102, a top bearing 104, a bottom bearing 106, a central shaft 108 and a first magnetic coupling plate 110. In turn, the base 70 includes a top plate 120 and a corresponding second magnetic coupling plate 122 coupled to a motor 124 through a rotating drive shaft 126. Fan assembly 72 is fluidly isolated from the motor 124, yet operably coupled to the motor 124 and drive shaft 126 to rotate therewith. Stated another way, the fan assembly 72 is operable such that fan 100 rotates with drive shaft 126 without fluid communicating contact between the fan 100 and drive shaft 126. In the embodiment illustrated, fan 100 is rotationally fixed to shaft 108 and magnetic plate 110 so as to rotate therewith with respect to housing 102, top bearing 104 and bottom bearing 106. In one embodiment, central shaft 108 is coaxial with drive shaft 126. Coupling plates 110 and 122 are spaced apart from one another such that a bottom side 128 of housing 102 is positioned between the plates 110 and 122. In one embodiment, a seal can be formed between bottom 128 of housing 102 and top plate 120 so as to further protect motor 124. In addition, top plate 120 defines an opening 129 to accommodate magnetic coupling plate 122. Bottom 128 of housing 102 is larger than opening 129 to provide further prevention of contamination reaching motor 124. In another embodiment, drive shaft 126 extends through top plate 120 such that coupling plate 122 is positioned above top plate 120, thereby providing further sealing of the motor 124. In this instance, opening 129 can be reduced in size so as to accommodate drive shaft 126 and, in yet a further embodiment, include a bearing to accommodate rotation of drive shaft 126.

Due to magnetic forces between coupling plates 110 and 122, fan 100 is configured to rotate as motor 124 is operated. As the motor 124 operates, the second magnetic coupling plate 122 rotates, causing rotation of the first magnetic coupling plate 110 and in turn the fan 100. In one embodiment, fan 100 is a squirrel-cage type fan operable to transfer gas from an inlet 130 in the housing 102 to an outlet 132 in the housing 102. Moreover, gas transferred within the fan assembly 72 is fluidly isolated from motor 124 as well as ambient air so as to prevent contaminants from entering within system 10. Fan 100 is concentrically arranged about shaft 108 and shaft 108 is positioned within bearings 104 and 106 to maintain shaft 108 in an upright position as fan 100 rotates. In one embodiment, both first coupling plate 110 and second coupling plate 122 include three rotationally spaced (e.g., separated by) 120° magnets that attract coupling plates 110 and 122 together. In another embodiment, more or fewer magnets can be utilized. Even if the corresponding magnets are misaligned upon placement of fan assembly 70 onto base 72, rotation of coupling plate 122 will align its magnets with corresponding magnets on coupling plate 110.

The attractive force between corresponding magnets is sufficient to rotate plates 110 and 122 together yet also allows fan assembly 72 to be easily removed from base 70 for cleaning. Once removed from base 70, fan assembly 72 can be replaced or soaked in a disinfectant in order to prevent cross-contamination for subsequent tests in rebreathe system 10. Additionally, to dry fan assembly 72 once subject to soaking, fan assembly 72 can be re-positioned to base 70. Motor 124 can then be operated to facilitate drying of fan assembly 72.

Although the present disclosure has been described with reference to preferred embodiments, workers skilled in the art will recognize that changes can be made in form and detail without departing from the spirit and scope of the present disclosure.

What is claimed is:

1. A rebreathe system for pulmonary function testing, comprising:
   a breathing valve assembly configured to be fluidly coupled to a patient;
   a flow control assembly coupled to the breathing valve assembly, the flow control assembly comprising an expire-only valve and an inspire-only valve, wherein when a rebreathe test is active, a gas exhaled by the patient flows out only through the expire-only valve and gas inhaled by the patient is provided only through the inspire-only valve;
   a reservoir coupled to the expire-only valve and configured to receive the exhaled gas from the expire-only valve;
   a carbon dioxide absorber comprising an outlet coupled only to the inspire-only valve of the flow control assembly and an inlet; and
   a circulation system, comprising:
      a base comprising a motor coupled to a first magnetic coupling plate; and
      a fan assembly coupled to the base and comprising:
         a housing comprising an inlet coupled to the reservoir and an outlet coupled to the inlet of the absorber;
         a fan disposed within the housing and fluidly isolated from the motor; and
         a second magnetic coupling plate fixedly coupled to the fan and magnetically coupled to the first magnetic coupling plate, wherein operation of the motor rotates the fan so as to pull the exhaled gas from the reservoir and push the exhaled gas through the absorber.

2. The rebreathe system of claim 1, wherein the fan is a centrifugal fan.

3. The rebreathe system of claim 1, wherein a bottom of the housing is positioned between the first magnetic coupling plate and the second magnetic coupling plate.

4. The rebreathe system of claim 1, wherein the base includes a top plate defining an opening configured to accommodate the second magnetic coupling plate, the bottom covering the opening.

5. The rebreathe system of claim 1, wherein the fan assembly further includes a central shaft, the fan being rotatable about the central shaft.

6. The rebreathe system of claim 5, wherein the fan assembly further includes at least one bearing coupled to the housing and the central shaft such that the central shaft rotates within the bearing.

7. The rebreathe system of claim 1, wherein the reservoir comprises a bag for storing exhaled gas.

8. A method of performing a pulmonary function test, the method comprising the steps of:
   receiving exhaled gas from a patient through an expire-only valve and into a reservoir; and
   operating a circulation system to draw the exhaled gas from the reservoir and push the exhaled gas through a carbon dioxide absorber, through an inspire-only valve, and directly to the patient, the circulation system comprising a base comprising a motor and a fan assembly comprising a housing, a fan disposed within the housing and fixedly coupled to a first magnetic coupling plate and the motor fixedly coupled to a second magnetic coupling plate that is magnetically coupled to the first magnetic coupling plate, such that, upon operation of the motor, the fan rotates.

9. The method of claim 8, wherein the fan is a centrifugal fan.

10. The method of claim 8, wherein a bottom of the housing is positioned between the first magnetic coupling plate and the second magnetic coupling plate.

11. The method of claim 8, wherein the base includes a top plate defining an opening configured to accommodate the second magnetic coupling plate, the bottom covering the opening.

12. The method of claim 8, wherein the fan assembly further includes a central shaft, the fan being rotatable about the central shaft.

13. The method of claim 12, wherein the fan assembly further includes at least one bearing coupled to the housing and the central shaft such that the central shaft rotates within the bearing.

14. The method of claim 8, wherein the reservoir comprises a bag for storing exhaled gas.

\* \* \* \* \*